United States Patent
Ahn

(10) Patent No.: US 10,398,212 B2
(45) Date of Patent: Sep. 3, 2019

(54) TOOLS, KITS, AND METHODS FOR ADJUSTING ARTIFICIAL EYELASHES

(71) Applicant: Kiss Nail Products, Inc., Port Washington, NY (US)

(72) Inventor: Ki Chul Ahn, Jericho, NY (US)

(73) Assignee: Kiss Nail Products, Inc., Port Washington, NY (US)

( * ) Notice: Subject to any disclaimer, the term of this patent is extended or adjusted under 35 U.S.C. 154(b) by 691 days.

(21) Appl. No.: 14/831,263

(22) Filed: Aug. 20, 2015

(65) Prior Publication Data

US 2017/0049172 A1 Feb. 23, 2017

(51) Int. Cl.
*A45D 40/30* (2006.01)
*A41G 5/02* (2006.01)
*A61B 5/107* (2006.01)
*G01B 3/00* (2006.01)

(52) U.S. Cl.
CPC ............. *A45D 40/30* (2013.01); *A41G 5/02* (2013.01); *A61B 5/1072* (2013.01); *G01B 3/006* (2013.01)

(58) Field of Classification Search
CPC .......... A45D 40/30; A41G 5/02; A61B 5/107; A61B 5/1072

USPC .................. 132/216, 319; 33/512
See application file for complete search history.

(56) References Cited

U.S. PATENT DOCUMENTS

| | | | | |
|---|---|---|---|---|
| 1,974,825 A * | 9/1934 | Lovie | ..................... | A45D 40/30 132/216 |
| 3,517,673 A * | 6/1970 | Kim | ....................... | A41G 5/02 132/214 |
| 3,557,653 A * | 1/1971 | Kim | ....................... | A41G 5/02 132/56 |
| 4,118,870 A * | 10/1978 | Dyson | ................... | A45D 40/30 33/512 |
| 2004/0231688 A1* | 11/2004 | Thayer | ................. | A45D 40/30 132/216 |
| 2007/0006748 A1* | 1/2007 | Liu | ....................... | A45D 40/30 101/127 |
| 2014/0069448 A1* | 3/2014 | Forsythe | ............... | A45D 40/30 132/200 |

* cited by examiner

*Primary Examiner* — Tatiana L Nobrega
(74) *Attorney, Agent, or Firm* — Venable LLP; Tamatane J. Aga; Elizabeth C. G. Gitlin

(57) ABSTRACT

The present disclosure relates to tools, kits, and methods for adjusting artificial eyelashes. The tool includes a body portion, a flange coupled to the body portion, and a plurality of indicia on the flange for measuring a lateral length of an individual's eyelashes.

21 Claims, 5 Drawing Sheets

TOOLS, KITS, AND METHODS FOR ADJUSTING ARTIFICIAL EYELASHES

FIELD OF TECHNOLOGY

The present disclosure relates generally to cosmetic applications, and, more particularly, to tools, kits, and methods for adjusting artificial eyelashes.

BACKGROUND

As an alternative to or in addition to mascara, eyelash lengthening, darkening or thickening may be accomplished by attaching artificial eyelashes to a user's eyelids to enhance the appearance of eyelashes. In a typical application, the set of artificial eyelashes may be cut, trimmed, or otherwise adjusted to the lateral length of the user's eyelashes. Such artificial eyelashes are generally secured to the user's eyelids by an adhesive.

SUMMARY

The present disclosure, in part, is directed to tools, kits, and methods for adjusting artificial eyelashes that address certain of the limitations of conventional approaches for adjusting artificial eyelashes. In conventional processes, retrieving the artificial eyelashes and adjusting the lateral length of the artificial eyelashes to the lateral length of the user's eyelashes can be difficult or cumbersome. For example, the user may grip the artificial eyelashes by the fingers, position the artificial eyelashes in proximity to the user's eyelashes in front of a mirror for comparing against the lateral length of the user's eyelashes, and then make proper adjustments to the artificial eyelashes. This process may be time-consuming, particularly, if the user needs to repeatedly make incremental adjustments to the artificial eyelashes. This is also inefficient because an incorrect adjustment to a set of artificial eyelashes may lead to that set going unused. Moreover, an inexperienced user may unintentionally end up damaging the artificial eyelashes by repeatedly retrieving and adjusting the artificial eyelashes. This is particularly true considering that the artificial eyelash strands can be delicate and small. For example, some artificial eyelash strands can be between approximately 0.01 mm and approximately 0.40 mm in diameter, and between approximately 2 mm and approximately 30 mm in length. Thus, there has developed a need for a tool for artificial eyelashes that can make measuring and trimming the artificial eyelashes quick, reliable, and user-friendly, which may potentially be also used as an applicator for such artificial eyelashes.

One non-limiting aspect of the present disclosure is directed to a measuring tool for a set of artificial eyelashes including a body portion, a flange coupled to the body portion, and at least one indicium on the flange for measuring a lateral length of an individual's eyelashes. In another aspect of the present disclosure, this measuring tool may also be used as an applicator for artificial eyelashes.

Another non-limiting aspect of the present disclosure is directed to a kit for adjusting a set of artificial eyelashes. The kit includes a packaging tray, and at least one measuring tool, which may also be used as an applicator for the set of artificial eyelashes, removably coupled to the packaging tray. The at least one measuring tool includes a body portion, a flange coupled to the body portion, and at least one indicium on the flange for measuring a lateral length of an individual's eyelashes.

Another non-limiting aspect of the present disclosure is directed to a method of adjusting a set of artificial eyelashes, the method including positioning a measuring tool, which may also be used as an applicator, in proximity to an individual's eyelashes, and measuring the lateral length of the individual's eyelashes. The measuring tool includes a body portion, a flange coupled to the body portion, and at least one indicium on the flange for measuring a lateral length of the individual's eyelashes. The set of artificial eyelashes is trimmed to the measured lateral length of the individual's eyelashes.

BRIEF DESCRIPTION OF THE DRAWINGS

The above and other aspects, features and advantages of the present disclosure will be more apparent from the following detailed description when taken in conjunction with the accompanying drawings, in which.

Figure 1:
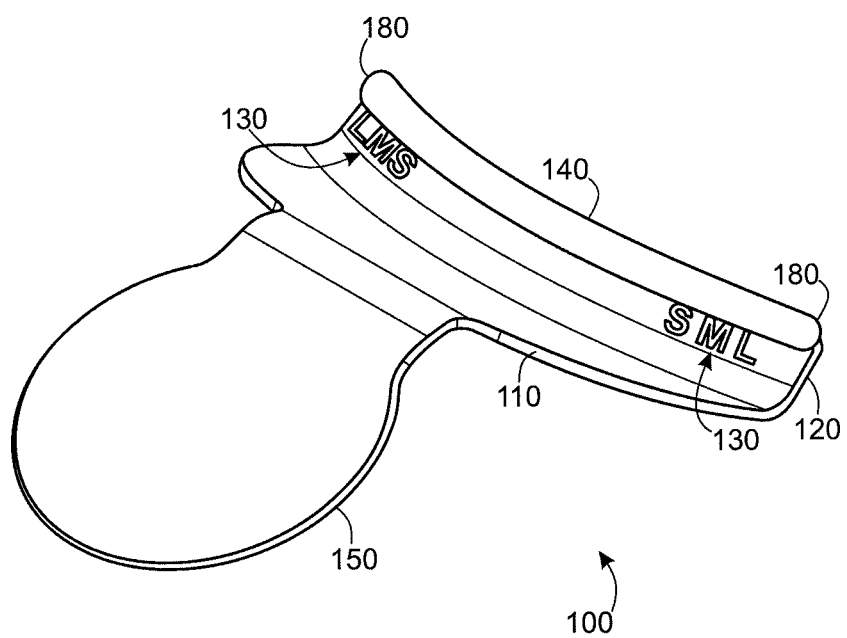
FIG. 1 is a perspective view of a measuring tool according to a non-limiting embodiment of the present disclosure including a plurality of indicia.

The reader will appreciate the foregoing details, as well as others, upon considering the following detailed description of certain non-limiting embodiments of tools, kits, and methods according to the present disclosure. The reader also may comprehend certain of such additional details upon using the tools, kits, and methods described herein.

DETAILED DESCRIPTION

Embodiments of the present disclosure are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the present disclosure. Further, in the following description of the present disclosure, various specific definitions found in the following description are provided only to provide a general understanding of the present disclosure, and it is apparent to those skilled in the art that the present disclosure can be implemented without such definitions.

The present disclosure, in part, is directed to tools, kits, and methods for adjusting artificial eyelashes that address certain of the limitations of conventional approaches for adjusting artificial eyelashes. "Artificial eyelashes" as used herein refers to a device including a plurality of strands that are not part of an individual's body for application to the eyelid. In certain non-limiting embodiments, the strands are coupled to a spine or base strand. In certain other non-limiting embodiments, the strands are not coupled to a spine or base strand, and are applied individually and directly to an individual's eyelid and/or eyelashes. The artificial eyelashes can be made from strands that may have been cleaned and dried, by tying the strands to a spine or base strand, trimming the strands to desired lengths, and curling the strands to provide a natural look.

Figure 2:
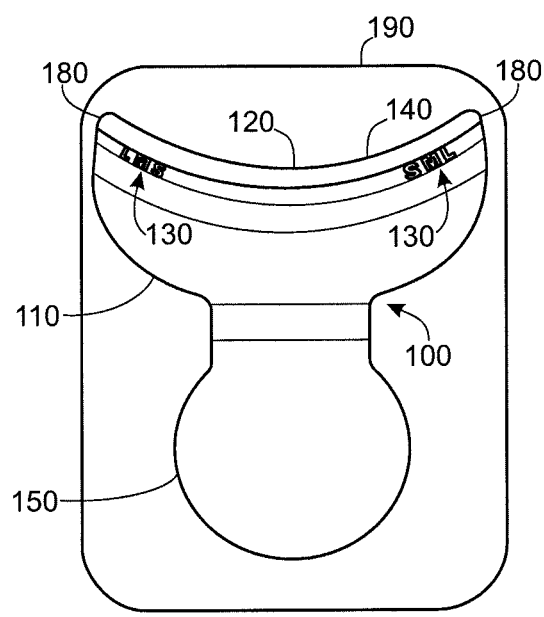
FIG. 2 is a plan view of the a measuring tool shown in FIG. 1.
Figure 3:
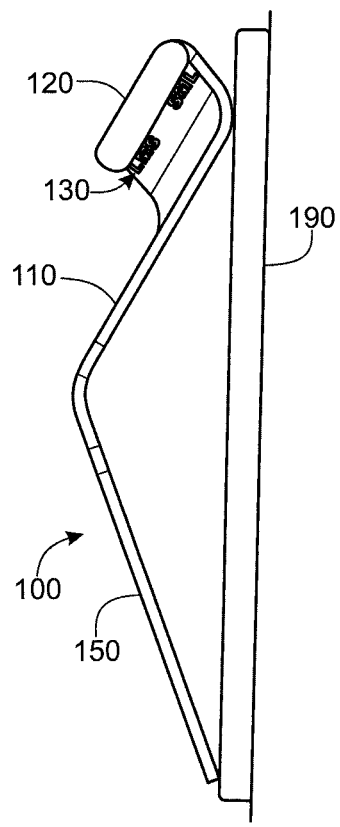
FIG. 3 is a side view of the a measuring tool shown in FIG. 1.

Referring to FIGS. 1-3, a non-limiting embodiment of a measuring tool 100 is illustrated. The measuring tool 100 includes a body portion 110, a flange 120 coupled to the body portion 110, and at least one indicium 130 on the flange 120 for measuring a lateral length of an individual's eyelashes (e.g., at least a portion of the distance between one crescent tip of the eye and the other crescent tip of the eye). The flange 120 has a slight curvature defining a concave arc 140 (see also FIG. 4), which mimics the curvature of a user's eyelid. The measuring tool 100 may be composed of a lightweight material such as paper, cardboard, or thin plastic. The body portion 110 can include a middle section, a first end section and a second end section provided opposite to the first end section, whereas the middle section has a first planar surface that extends into the first end section at a first angle so as to form a first apex. The first angle forming the first apex can be provided closest to a proximal-most terminal edge of the flange 120.

According to certain non-limiting embodiments, the body portion 110 is coupled with at least one leg 150 opposite the flange 120. The leg(s) 150 can have a second planar surface that (i) extends from a distal-most terminal edge of the leg 150, and (ii) is coupled to the second end section of the body portion 110 at a second angle, whereas the first and second planar surfaces can extend in different directions, and whereas the leg(s) 150 can be configured to be held by a user during a measuring operation by the measuring tool. The distal-most terminal edge of the leg 150 can be provided on an opposite end of the measuring tool 100 from the proximal-most terminal edge of the flange 120, and the first apex and the second apex point to opposite directions. Although the embodiments of the present disclosure describe a specific configuration of one leg 150 extending from the body portion 110 of the measuring tool 100, any number or configuration of legs may be used that allow for proper positioning of the measuring tool 100. For example, embodiments of the present disclosure can include a measuring tool having side legs in addition to the leg 150.

The measuring tool 100 can generally have a wishbone shape due to the curvature of the flange 120 and the width of the leg 150. According to certain non-limiting embodiments, the body portion 110 is substantially planar, and the leg 150 is angled away from the body portion 110. According to certain non-limiting embodiments, the leg 150 is angled away from the body portion 110 at approximately 30 degrees to approximately 60 degrees. The wishbone shape of the measuring tool 100 and the angled disposition of the leg 150 can prevent a user's hand from interfering with the vision of the user, when the measuring tool 100 is being used to measure the lateral length of the individual's eyelashes. Therefore, the measuring tool 100 can facilitate easily and conveniently measuring the lateral length of the individual's eyelashes, as further detailed below. Other configurations are possible depending on the usage requirement or preferences for the particular measuring tool 100, including configurations where the leg 150 is substantially parallel to the body portion 110.

Figure 4:
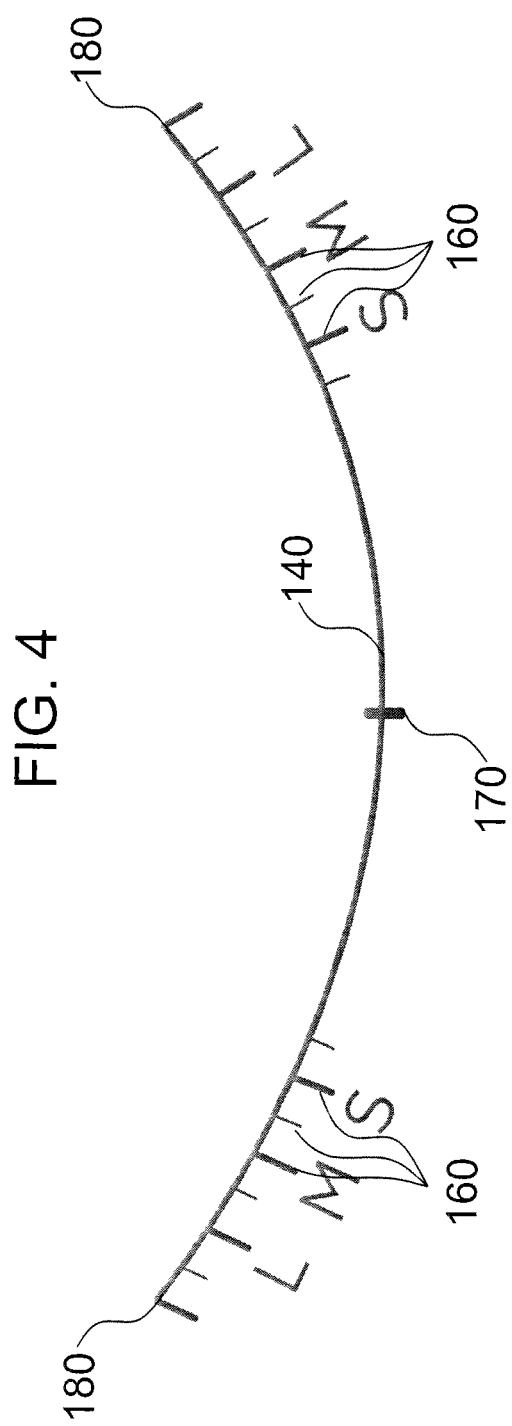
FIG. 4 is an enlarged view of the plurality of indicia shown in FIG. 1.

Referring also to FIG. 4, according to the illustrated non-limiting embodiment, the at least one indicium 130 comprises a plurality of lines 160 extending perpendicular to the concave arc 140. According to certain non-limiting embodiments, the flange 120 defines a centerline 170 perpendicular to the concave arc 140, and the lines 160 are positioned to at least one side of the centerline 170. Stated differently, the lines 160 are off-center when viewed along a direction perpendicular to the concave arc 140. According to certain non-limiting embodiments, the lines 160 are positioned symmetrically relative to the center 170. According to certain non-limiting embodiments, the at least one indicium 130 comprises up to ten lines on one side of the centerline 170. For example, the indicia 130 may include two or more, three or more, four or more, five or more, six or more, seven or more, eight or more, or nine or more lines on one side of the centerline 170. According to certain non-limiting embodiments, the arc 140 of the flange 120 defines two endpoints 180, and the at least one indicium 130 is positioned at least two-thirds of a distance from the centerline 170 to the end points 180.

According to certain non-limiting embodiments, the at least one indicium 130 is associated with at least one of a number (e.g., "1," "2," or "3"), a letter (e.g., "S," "M," or "L"), and a symbol (e.g., "○" or "▲"). According to certain non-limiting embodiments, the indicia 130 are configured to indicate small, medium, and large. The at least one indicium 130 can assume any of a virtually unlimited variety of numbers, letters, alphanumerics, colors, shapes, designs, or combinations of any of these, for example, so long as they are at least one side of the centerline 170 for measuring a lateral length of an individual's eyelashes. Upon considering the present description, those having ordinary skill may readily design or identify other possible indicia that can be used to measure a lateral length of an individual's eyelashes according to the present disclosure.

According to certain non-limiting embodiments, the measuring tool 100 is removably coupled to a packaging tray 190. In further embodiments, the measuring tool 100 is coupled to the packaging tray 190 through at least one frangible joint, and is removable from the packaging tray 190 when the at least one frangible joint is broken. For example, the measuring tool 100 may be attached to the packaging tray 190 via glue or friction.

Figure 5:
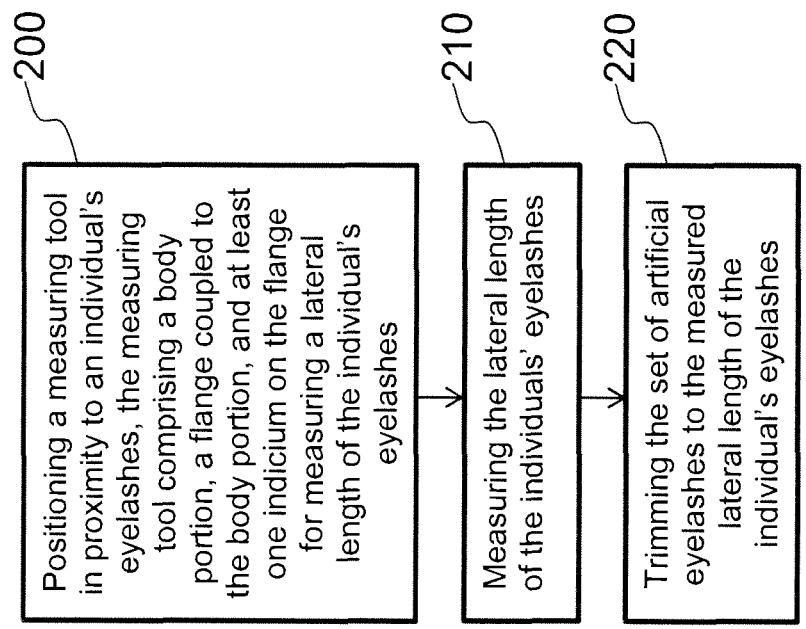
FIG. 5 is a flow chart of a non-limiting embodiment of a method of adjusting a set of artificial eyelashes according to the present disclosure.

Referring also to FIG. 5, to adjust a set of artificial eyelashes with the measuring tool 100, the measuring tool 100 is positioned in proximity to an individual's eyelashes (block 200), and the lateral length of the individual's eyelashes is measured (block 210). In this regard, the indicia 130 comprising the plurality of lines 160 disclosed herein may resemble and operate like a ruler. The set of artificial eyelashes is then trimmed to the measured lateral length of the individual's eyelashes (block 220). According to certain non-limiting embodiments, the measuring tool 100 may also be used as an applicator for the set of artificial eyelashes. In other embodiments, the artificial eyelashes may be applied using a separate applicator. According to certain non-limiting embodiments, the measuring tool 100 can be used for measuring the lateral length of an individual's eyebrows, e.g., for trimming the eyebrows to an optimal length.

While the invention has been shown and described with reference to certain embodiments thereof, it will be understood by those skilled in the art that various changes in form and detail may be made therein without departing from the spirit and scope of the invention as defined by the appended claims and their equivalents.

The invention claimed is:

1. An eyelash measuring tool for measuring a lateral length of an individual's eyelashes, comprising:
   a single leg defining a terminal distal end of the eyelash measuring tool, the leg having a circular shape except in a proximal-most portion thereof, where the proximal-most portion extends linearly in a proximal direction away from the terminal distal end, the leg providing planar opposing surfaces and being inclined such that the proximal-most portion of the leg is disposed vertically above the terminal distal end, when viewed from a side view of the tool;

a body portion extending from the proximal-most portion of the leg and having a middle section, a first end section and a second end section provided opposite to the first end section, wherein the second end section extends directly from the proximal-most portion of the leg and the middle section has a first planar surface, the body portion is inclined such that the second end section is disposed vertically above the first end section, when viewed from the side view; and a flange portion extending distally from the first end section of the body portion, the flange portion defines a terminal proximal end of the eyelash measuring tool and the terminal proximal end forms a concave arc configured to engage a curvature of a user's eyelid, wherein the flange portion is inclined such that the terminal proximal end of the flange portion is disposed vertically above a distal end of the flange portion located immediately adjacent the first end section of the body portion, when viewed from the side view;

indicia provided symmetrically on opposing end portions of the flange portion for measuring a lateral length of eyelashes of the individual;

wherein a first apex is formed where the first end section of the body portion and the terminal proximal end of the flange portion are joined and a second apex is formed where the proximal-most portion of the leg and the second end section of the body portion are joined and the first apex and the second apex point in opposite directions such that when the tool is placed on a flat support surface, the terminal distal end and the first apex contact the flat support surface, the first apex points downwardly toward the flat support surface and the second apex points upwardly away from the flat support surface, the leg is configured to be held by a user during a measuring operation by the eyelash measuring tool, and wherein, when viewed from a top view, the eyelash measuring tool provides a longitudinal axis extending along a center of the eyelash measuring tool between opposing terminal proximal and distal ends thereof, and the leg, the body portion and the flange portion each have a width which extends in a direction transverse to the longitudinal axis, the tool providing a smallest width at the second apex and the proximal-most portion of the leg, a maximum width of the leg is defined by a diameter of the circular shape thereof and the body portion has arched lateral side which taper in width toward the second end section where a maximum width of the body portion is larger than the maximum width of the leg.

2. The eyelash measuring tool of claim 1, wherein a first angle is formed at the first apex, and wherein the first angle extends in a first direction which is opposite to a second direction of extension of a second angle formed at the second apex.

3. The eyelash measuring tool of claim 2, wherein a direction of extension of the first end section along a planar surface thereof is different from a direction of extension of a free end of the leg which is substantially straight along a planar surface thereof.

4. The eyelash measuring tool of claim 1, wherein the body portion is planar.

5. The eyelash measuring tool of claim 1, wherein the indicia comprise a plurality of lines extending perpendicular to the concave arc.

6. The eyelash measuring tool of claim 5, wherein the flange portion defines a centerline perpendicular to the concave arc, and the lines are positioned symmetrically relative to the centerline.

7. The eyelash measuring tool of claim 6, wherein indicia comprise up to ten lines on each side of the centerline.

8. The eyelash measuring tool of claim 1, wherein the concave arc of the flange portion defines two endpoints, and the indicia are positioned at least two-thirds of a distance from a centerline to each of the two endpoints.

9. The eyelash measuring tool of claim 1, wherein the indicia are associated with at least one of a number, a letter, and a symbol.

10. The eyelash measuring tool of claim 9, wherein the at least one of a number, a letter, and a symbol is configured to indicate small, medium, or large.

11. A kit for adjusting a set of artificial eyelashes, the kit comprising:

a packaging tray; and at least one eyelash measuring tool removably coupled to the packaging tray, the at least one eyelash measuring tool comprising:

a single leg defining a terminal distal end of the eyelash measuring tool, the leg having a circular shape except in a proximal-most portion thereof, where the proximal-most portion extends linearly in a proximal direction away from the terminal distal end, the leg providing planar opposing surfaces and being inclined such that the proximal-most portion of the leg is disposed vertically above the terminal distal end, when viewed from a side view of the tool;

a body portion extending form the proximal-most portion of the leg and having a middle section, a first end section and a second end section provided opposite to the first end section, wherein the second end section extends directly from the proximal-most portion of the leg and the middle section has a first planar surface, the body portion is inclined such that the second end section is disposed vertically above the first end section, when viewed from the side view;

a flange portion extending distally from the first end section of the body portion, the flange portion defines a terminal proximal end of the eyelash measuring tool and the terminal proximal end forms a concave arc configured to engage a curvature of a user's eyelid, wherein the flange portion is inclined such that the terminal proximal end of the flange portion is disposed vertically above a distal end of the flange portion located immediately adjacent the first end section of the body portion, when viewed from the side view; and indicia provided symmetrically on opposing end portions of the flange portion for measuring a lateral length of eyelashes of a individual;

wherein a first apex is formed where the first end section of the body portion and the terminal proximal end of the flange portion are joined and a second apex is formed where the proximal-most portion of the leg and the second end section of the body portion are joined and the first apex and the second apex point in opposite directions such that when the tool is placed on a flat support surface, the terminal distal end and the first apex contact the flat support surface, the first apex points downwardly toward the flat support surface and the second apex points upwardly away from the flat support surface, the leg is configured to be held by a user during a measuring operation by the eyelash measuring tool, and wherein, when viewed from a top view, the eyelash measuring tool provides a longitudinal axis extending along a center of the eyelash measuring tool between opposing terminal proximal and distal ends thereof, and the leg, the body portion and the flange portion each have a width which extends in a direction transverse to the longitudinal axis, the tool providing a smallest width at the second apex and the proximal-most portion of the leg, a maximum width of the leg is defined by a diameter of the circular shape thereof and the body portion has arched lateral side which taper in width toward the second end section where a maximum width of the body portion is larger than the maximum width of the leg.

12. The kit of claim 11, wherein a first angle is formed at the first apex, and wherein the first angle extends in a first direction which is opposite to a second direction of extension of a second angle formed at the second apex.

13. The kit of claim 12, wherein a direction of extension of the first end section along a planar surface thereof is different from a direction of extension of a free end of the leg which is substantially straight along a planar surface thereof.

14. The kit of claim 11, wherein the body portion is planar.

15. The kit of claim 11, wherein the indicia comprise a plurality of lines extending perpendicular to the concave arc.

16. The kit of claim 15, wherein the flange portion defines a centerline perpendicular to the concave arc, and the lines are positioned symmetrically relative to the centerline.

17. The kit of claim 16, wherein the indicia comprise up to ten lines on each side of the centerline.

18. The kit of claim 11, wherein the concave arc of the flange portion defines two endpoints, and the indicia are positioned at least two-thirds of a distance from a centerline to each of the two endpoints.

19. The kit of claim 11, wherein the indicia are associated with at least one of a number, a letter, and a symbol.

20. The kit of claim 19, wherein the at least one of a number, a letter, and a symbol is configured to indicate small, medium, or large.

21. A method of adjusting a set of artificial eyelashes, the method comprising:

positioning the eyelash measuring tool according to claim 1 in proximity to an individual's eyelashes;

measuring the lateral length of the individual's eyelashes; and trimming the set of artificial eyelashes to the measured lateral length of the individual's eyelashes.

* * * * *